United States Patent [19]
Frey et al.

[11] Patent Number: 5,491,267
[45] Date of Patent: Feb. 13, 1996

[54] ETHERIFICATION PROCESS USING POST SEPARATION RECYCLE

[75] Inventors: Stanley J. Frey; David W. Liu, both of Palatine; Charles P. Luebke, Mount Prospect; Terry L. Marker, Palatine, all of Ill.

[73] Assignee: UOP, Des Plaines, Ill.

[21] Appl. No.: 207,525

[22] Filed: Mar. 7, 1994

Related U.S. Application Data

[63] Continuation-in-part of Ser. No. 10,896, Jan. 29, 1993, abandoned.

[51] Int. Cl.$^6$ .................................................. C07C 43/02
[52] U.S. Cl. ........................................................ 568/647
[58] Field of Search .............................................. 568/697

[56]          References Cited
         U.S. PATENT DOCUMENTS

| | | | |
|---|---|---|---|
| 3,629,478 | 8/1969 | Haunschild | 260/677 A |
| 3,634,534 | 8/1969 | Haunschild | 260/677 A |
| 3,634,535 | 8/1969 | Haunschild | 260/677 A |
| 4,182,913 | 1/1980 | Takezono et al. | 568/697 |
| 4,250,052 | 2/1981 | Smith, Jr. | 252/426 |
| 4,310,710 | 1/1982 | Torck et al. | 568/597 |
| 4,336,407 | 6/1982 | Smith, Jr. | 568/697 |
| 4,413,150 | 11/1983 | Briggs | 568/697 |
| 5,015,782 | 5/1991 | Harandi et al. | |

Primary Examiner—Johann Richter
Assistant Examiner—John Peabody
Attorney, Agent, or Firm—Thomas K. McBride; John F. Spears, Jr.; Reginald K. Taylor

[57]          ABSTRACT

In a process for the production of tertiary ethers by the reaction of an alcohol and isoalkene, a sidecut stream is selected from the etherification separation zone and recycled back to the etherification reaction zone. When this sidecut stream is characterized by an isoalkene to tertiary ether molar concentration ratio that is greater than the isoalkene to tertiary ether molar concentration ratio of the etherification reaction effluent (which is normally at equilibrium conditions), the conversion of isoalkene to tertiary ether is increased.

2 Claims, 3 Drawing Sheets

ETHERIFICATION PROCESS USING POST SEPARATION RECYCLE

CROSS REFERENCE TO RELATED APPLICATION

This application is a continuation-in-part of prior application Ser. No. 08/010,896 filed Jan. 29, 1993 now abandoned, the teachings of which are incorporated by reference.

FIELD OF THE INVENTION

The present invention relates to a process for the production of an ether by the reaction of an alcohol with an isoolefin. More specifically, this invention relates to a process for the production of ether using post distillation recycle of a stream comprising unreacted isoolefin and ether product to the etherification reaction zone.

BACKGROUND OF THE INVENTION

Oxygenates, such as ethers, have been a part of the U.S. gasoline strategy since the late 1970's. These materials reduce carbon monoxide emissions and unburned hydrocarbons in the exhaust of internal combustion engines. Another advantage of oxygenates is that they have relatively good blending characteristics. Some oxygenates have better blending characteristics than others. For example, the blending vapor pressures of methyl tertiary butyl ether (MTBE), ethyl tertiary butyl ether (ETBE), and tertiary amyl methyl ether (TAME) are lower than methanol and ethanol making them more attractive gasoline components.

MTBE is produced by contacting isobutylene with methanol over an acidic ion exchange resin catalyst. The reaction is exothermic and is conducted in a liquid phase at moderate temperatures. The operating pressure is chosen in order to maintain the reaction in the liquid phase. Major sources of isobutylene feedstock are derived from catalytic cracking and ethylene cracking. Since isobutylene is a by-product of these processes its supply is limited. While in the past MTBE production has depended largely on the availability of isobutylene from refinery operations, isobutylene is available from other sources. For example, isobutylene can be produced by dehydrating tertiary butyl alcohol (TBA). Isobutylene can also be produced by: (1) dehydrogenating isobutane; (2) isomerizing mixed butenes to isobutylene; or (3) isomerizing mixed butenes to isobutane and then dehydrogenating to isobutylene. These methods of producing isobutylene have proven to be very expensive.

Side reactions that occur in the MTBE reaction zone include (1) the reaction of isobutene with water to form tertiary butyl alcohol (TBA); (2) reaction of one methanol molecule with another methanol molecule to form dimethyl ether (DME) and water; and (3) the reaction of one isobutylene molecule with another isobutylene molecule to form di-isobutylene (DIB).

TAME is produced by reacting methanol with tertiary olefins having five carbon atoms (isoamylenes). As a result, there is an improvement of the octane value of the $C_5$ olefinic fractions. The octane is increased by four octane numbers, the olefinic content is reduced by a factor of 2, and motor fuel production from the $C_5$ fraction is increased by 7%. The main sources of isoamylenes are steam-cracked and light FCC gasolines. The isoamylene content of a stabilized steam-cracked $C_5$ cut and an FCC $C_5$ cut are 25 wt. % and 30 wt. %, respectively.

Side reactions that can occur in the TAME reaction zone include: (1) the reaction of one isoamylene molecule with another isoamylene molecule to form diisoamylene (DIA); (2) the reaction of one methanol molecule with another methanol molecule to form di-methyl ether (DME) and water; and (3) the reaction of isoamylene with water to form tertiary amyl alcohol (TAA).

Although the reactions and side reactions of MTBE and TAME may appear similar, the equilibrium and kinetics for the formation of MTBE and TAME are strikingly different. The reaction rate constants for TAME are found to be generally less than 50% of the reaction rates for MTBE. Even more significant is the change in equilibrium. Because of this equilibrium difference, the preparation of MTBE from stoichiometric proportions of isobutene and methanol can achieve conversions between 85% and 100%, whereas comparable preparations of TAME have been found to achieve conversions of only 50% to 60%.

The equilibrium conversion for alkyl methyl ethers was significantly improved by the application of reactive distillation technology to the etherification process, i.e., simultaneous etherification and separation by distillation of the etherification product. Reactive distillation is especially suited to the production of alkyl methyl ethers by the reaction of alcohols and isoolefins because the conversion rates for these reactions are equilibrium limited, particularly the TAME reaction. By removing the alkyl methyl ether product from the reaction zone as soon as it is produced, more alkyl methyl ether product is produced, thereby increasing the conversion of isoolefins to ethers.

The application of reactive distillation to etherification was first disclosed in the Haunschild patents (U.S. Pat. Nos. 3,629,478, 3,634,534, and 3,634,535). It was later commercialized using a specific type of catalyst structure disclosed in U.S. Pat. Nos. 4,336,407 and 4,250,052.

U.S. Pat. No. 4,413,150 (Briggs) discloses an etherification process wherein isobutylene and methanol are fed into an etherification zone. The effluent from the etherification zone is sent to a fractionation column which splits the effluent stream into an overhead stream comprising isobutylene, methanol and some MTBE and a bottoms stream comprising MTBE. The overhead stream is taken off the fractionation column at a location above the point where the feed to the fractionation column is introduced and is recycled to the etherification reactor.

U.S. Pat. No. 4,182,913 (Takezono et al.) discloses a method for continuously producing MTBE in which isobutylene and methanol are reacted in the presence of an acidic cation exchange resin in an etherification reactor. The resulting effluent is neutralized and then passed to a separation column. At a location above the point where the feed to the separation column is introduced, an overhead stream comprising isobutylene is recycled to the etherification reactor.

U.S. Pat. No. 4,310,710 (Torck et al.) discloses a process for producing MTBE. In the first step, methanol and isobutylene are introduced into an etherification reactor to form an etherification effluent stream containing MTBE, isobutylene, and methanol. This effluent stream is passed to a fractionation column where a process stream containing isobutylene and MTBE is taken off at a location above the point where the feed to the fractionation column is introduced and recycled to the etherification reactor.

Nevertheless, there is still a need for higher conversion etherification processes, particularly in the case of TAME production.

SUMMARY OF THE INVENTION

It has been discovered that recycling a sidecut stream from an etherification effluent separation unit (for example, a distillation column) to a fixed bed etherification reactor can increase the conversion of isoalkenes to tertiary ethers. The sidecut stream is characterized by a Recycle Quotient of greater than one. The Recycle Quotient is a ratio of two other ratios. The numerator of the Recycle Quotient is the ratio of the molar concentration of isoalkene in the sidecut stream to the molar concentration of tertiary ether in the sidecut stream. The denominator of the Recycle Quotient is the ratio of the molar concentration of isoalkene in the etherification effluent to molar concentration of tertiary ether in the etherification effluent, which normally approaches the reaction equilibrium molar concentration ratio. By recycling such a sidecut stream to the etherification reactor, the conversion of isoalkene and alcohol to a tertiary ether can be significantly increased, particularly when the desired tertiary ether product is TAME.

The present invention is a process for the production of ether from a feed stream comprising an isoalkene isomer which process comprises the steps of: mixing an etherification zone input stream comprising the isoalkene isomer with a $C_1$–$C_5$ monohydroxy alcohol to produce a combined feed and contacting the combined feed with an etherification catalyst in a fixed-bed etherification zone at etherification conditions to react the isoalkene isomer with the alcohol, thereby producing an etherification zone effluent stream comprising the ether and unreacted isoalkene isomer; passing at least a portion of a separation zone input stream comprising the etherification zone effluent stream to a separation zone; withdrawing an etherification zone sidecut stream from the separation zone at a point below where the separation zone input stream is introduced to the separation zone, the etherification zone sidecut stream being characterized by the following expression:

$$\text{Recycle Quotient} = \frac{\frac{I' \text{ recy}}{E' \text{ recy}}}{\frac{I' \text{ eq}}{E'' \text{ eq}}} > 1$$

where:

I recy=molar concentration of isoalkene in the etherification sidecut stream

E recy=molar concentration of tertiary ether in the etherification sidecut stream I effl=molar concentration of isoalkene in the etherification effluent stream E effl=molar concentration of tertiary ether in the etherification effluent stream;

recycling at least a portion of the etherification zone sidecut stream to the etherification zone; and recovering the ether from the separation zone.

In one embodiment, the present invention is a process for the production of tertiary amyl methyl ether from a feed stream comprising isoamylene, isopentane, normal pentene, and normal pentane isomers, the process comprising the steps of: mixing an etherification zone input stream comprising the isoamylene isomer with methanol to produce a combined feed and contacting the combined feed with an etherification catalyst in an etherification zone at etherification conditions to react the isoamylene isomer with the methanol to equilibrium, thereby producing an etherification zone effluent stream comprising the tertiary amyl methyl ether, isoamylene, isopentane, normal pentene, and normal pentane isomers; passing at least a portion of a distillation zone input stream comprising the etherification zone effluent stream to a distillation zone; withdrawing an overhead raffinate stream from the distillation zone; withdrawing a bottoms product stream comprising tertiary amyl methyl ether from the distillation zone; withdrawing an etherification zone sidecut stream from the distillation zone at a point below where the distillation zone input stream is introduced to the distillation zone, the etherification zone sidecut stream being characterized by the following expression:

$$\text{Recycle Quotient} = \frac{\frac{I' \text{ recy}}{E' \text{ recy}}}{\frac{I' \text{ eq}}{E'' \text{ eq}}} > 1$$

where:

I' recy=molar concentration of isoamylene in the etherification sidecut stream

E' recy=molar concentration of TAME in the etherification sidecut stream

I' eq=equilibrium molar concentration of isoamylene in the etherification zone

E' eq=equilibrium molar concentration of TAME in the etherification zone;

recycling at least a portion of the etherification zone sidecut stream to the etherification zone; and recovering the tertiary amyl methyl ether from the distillation zone.

In another embodiment, the present invention is a process for the production of tertiary amyl methyl ether from a feed stream comprising isoamylene, isopentane, normal pentene, and normal pentane isomers, the process comprising the steps of: mixing an etherification zone input stream comprising the isoamylene isomer with methanol to produce a combined feed and contacting the combined feed with an etherification catalyst comprising a macroporous acid-form sulfonated solid resin in an etherification zone at etherification conditions to react the isoamylene isomer with the methanol and to produce a first etherification zone effluent stream comprising the tertiary amyl methyl ether, methanol, and isoamylene, isopentane, normal pentene, and normal pentane isomers; passing at least a portion of a distillation zone input stream comprising the first etherification zone effluent stream into a reactive distillation zone at a first point with the reactive distillation zone containing a bed of etherification catalyst comprising a macroporous acid-form sulfonated solid resin at etherification conditions to further react the isoamylene isomer with the methanol to equilibrium, thereby producing a second etherification zone effluent stream; withdrawing an overhead raffinate stream comprising isopentane and methanol from the reactive distillation zone; withdrawing a bottoms product stream comprising tertiary amyl methyl ether from the reactive distillation zone; withdrawing a vapor-phase sidecut stream from the reactive distillation zone at a second point below the first point, the vapor-phase sidecut stream being characterized by the following expression:

$$\text{Recycle Quotient} = \frac{\frac{I' \text{ recy}}{E' \text{ recy}}}{\frac{I' \text{ eq}}{E'' \text{ eq}}} > 1$$

where:

I' recy=molar concentration of isoamylene in the etherification sidecut stream

E' recy=molar concentration of TAME in the etherification sidecut stream

I'' eq=equilibrium molar concentration of isoamylene in the etherification zone

E" eq=equilibrium molar concentration of TAME in the etherification zone;

recycling the vapor-phase sidecut stream to the etherification zone; and recovering the tertiary amyl methyl ether from a bottoms stream of the reactive distillation zone.

In another embodiment, the present invention is a process for the production of a tertiary ether from a feed stream comprising an isoalkene isomer which process comprises the steps of: mixing an etherification zone input stream comprising the isoalkene isomer with a $C_1$–$C_5$ monohydroxy alcohol to produce a combined feed and contacting the combined feed with an etherification catalyst in an etherification zone at etherification conditions to react the isoalkene isomer with the alcohol, thereby producing an etherification zone effluent stream comprising the ether and unreacted isoalkene isomer; passing at least a portion of a fractionation column input stream comprising the etherification zone effluent stream to a separation zone; withdrawing a first fractionation column stream from the fractionation column at a point above where the fractionation column input stream is introduced to the separation zone; withdrawing a vapor-phase second fractionation column stream from the fractionation column at a point below where the fractionation column input stream is introduced to the fractionation column; withdrawing a third fractionation column stream from the fractionation column at a point below where the fractionation column stream is withdrawn from the fractionation column; recycling at least a portion of the second fractionation column stream to the etherification zone; and recovering the tertiary ether from the third fractionation column stream.

DESCRIPTION OF THE PREFERRED EMBODIMENT

Figure 1:
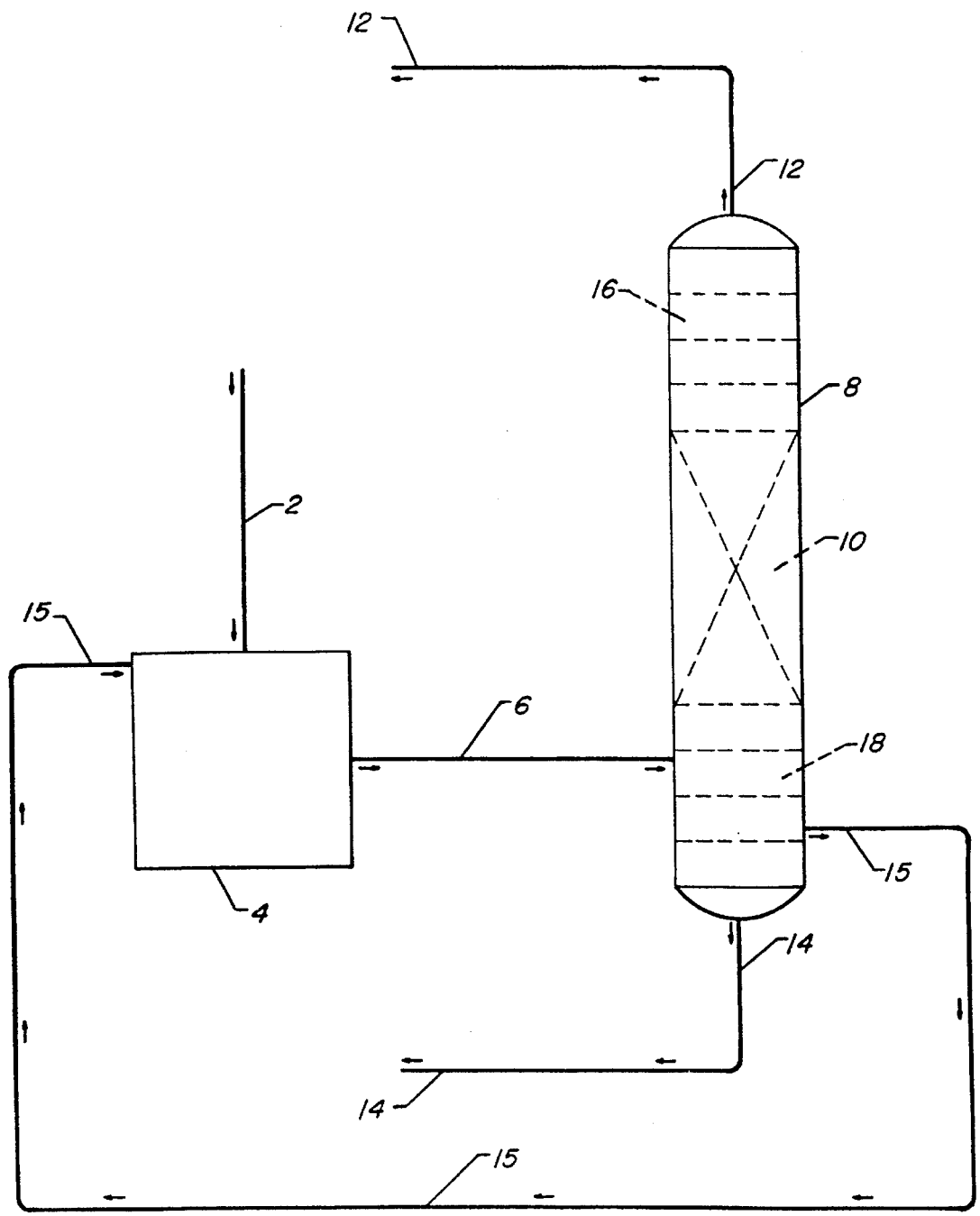
FIG. 1 shows a schematic illustration of a process of this invention.

The present invention is broadly applicable to the production of a wide variety of ethers from a number of different feedstocks. The primary ethers for which this invention will be applied are tertiary-amyl, tertiary-butyl and tertiary-hexyl ethers. Where the etherification process is one for the production of butyl ethers, the typical feed stream will consist of a mixture of $C_4$ isomers comprising isobutane, isobutene, normal butane, 1-butene and 2-butene. Where the process is one for the production of amyl ethers, the feed stream components will include 3-methyl-1-butene, isopentane, 1-pentene, 2-methyl-1-butene, normal pentane, trans-2-pentene, cis-2-pentene and 2-methyl-2-butene in a typical distribution of isomers. Although a variety of sources are available to provide such hydrocarbon feed streams, the most common sources for the feed streams for these processes are light cracked hydrocarbon streams from an FCC unit or a $C_4$ stream from a steam cracker after butadiene extraction. In a preferred embodiment, the etherification feedstream of the present invention comprises isoamylene, which can include both the reactive isomers (2-methyl-1-butene and 2-methyl-2-butene) and unreactive isomer (3-methyl-1-butene).

Often the FCC effluent will contain diolefins in addition to the desired monoolefin feed components. These diolefins interfere with the operation of the catalyst in downstream processes by polymerizing and forming heavy hydrocarbons that block the active sites of the catalyst and prevent their use. In a preferred embodiment, the hydrocarbon feed stream of the present invention can undergo treatment for the elimination of diolefins. A common method of eliminating diolefins is by the selective hydrogenation of the olefins to saturate the diolefins into monoolefins. Suitable catalysts and operating conditions for such a selective dehydrogenation process can be found in U.S. Pat. Nos. 4,695,560 and 4,734,540, the contents of which are hereby incorporated by reference.

The selective hydrogenation process typically employs a nickel on aluminum catalyst or a noble metal, such as palladium on alumina, for selective hydrogenation. The nickel may be sulfided or unsulfided. The process can also operate in a broad range of operating conditions including pressures of from about 40–800 psig with pressures of between 50–300 psig being preferred and temperatures of from about 70°–700° F. with temperatures of from about 120°–400° F. being preferred. Effective space velocities for the processes should be above 1 $hr^{-1}$ and preferably above 5 with a range of from about 5 to 35 $hrs^{-1}$. It is typical in such a process to limit the mount of hydrogen to prevent the saturation of monoolefins such that there is less than twice the stoichiometric mount of hydrogen required for the selective hydrogenation in the process. Preferably, the mole ratio of hydrogen to diolefinic hydrocarbons in the material will be in the range of from 1:1 to 1.8:1, and in some cases the hydrogen will be less than the stoichiometrically required amount of hydrogen The hydrocarbon feedstock of the present invention may also contain a variety of sulfur compounds. Generally, the feed stream contains about 1 to 5000 ppm by weight $H_2S$ and COS, more typically from about 1–1000 ppm by weight $H_2S$, calculated as elemental sulfur of the feedstock.

In one embodiment of the present invention, the hydrocarbon feedstock of the present invention is passed into an amine treating zone for $H_2S$ and COS removal. This amine treating zone employs alkanolamines selected from the group consisting of monoethanolamine (MEA), diethanolamine (DEA), methyldiethanolamine (MDEA), and mixtures thereof. The amine treating zone is operated over a temperature ranging from about 60°–150° F. and a pressure ranging from about 15–500 psia. The amine treating will provide an $H_2S$- and COS- depleted stream which has been reduced by about 90% and preferably reduced by about 95% of the $H_2S$ and COS originally in the hydrocarbon feed stream.

In a preferred embodiment, the hydrocarbon feedstock of the present invention can be passed to a mercaptan treating zone. In the mercaptan treating zone, the $H_2S$— and COS-depleted hydrocarbon feedstock is contacted with an alkaline scrubbing solution under mercaptan absorption conditions effective to produce a mercaptan-depleted stream and a mercaptide-containing scrubbing solution. The alkaline scrubbing solution may be selected from the group consisting of aqueous sodium hydroxide or aqueous ammonium hydroxide. The mercaptide-containing scrubbing solution is contacted with air or oxygen in the presence of an oxidation catalyst effective to regenerate the mercaptide-containing scrubbing solution. The temperature of the scrubbing solution ranges between about 10 and about 80° C., preferably between about 20° C. and about 60° C. and a pressure generally in the range of about 100 kPa absolute to about 3450 kPa absolute in order to keep the $H_2S$— and COS— depleted stream in the liquid phase.

Additional information on the preferred mercaptan treating zone of the present invention can be found in U.S. Pat. Nos. 4,908,122 and 4,913,802 which are hereby incorporated by reference.

The hydrocarbon feed stream of the present invention may also contain nitrogen compounds including ammonia, light amines, dimethylformamide, N-methylpyrolydone, and nitriles having 1 to 3 carbon atom, e.g., acetonitrile (ACN) and propionitrile. These nitrogen compounds can be removed from the hydrocarbon feed stream by passing the hydrocarbon feedstock of the present invention through a nitrogen removal zone, water wash zone, or a zone that performs hydrolysis to ammonia.

The feed to the process includes an alcohol to react with the isoolefin and produce the desired ether product. The alcohols that can be used are typically $C_1$–$C_5$ monohydroxy alcohols. Methanol typically constitutes the alcohol of choice for the etherification process. Ethanol, although used less often, is also a commonly available alcohol for the etherification process.

The alcohol will enter the etherification zone along with the isoalkene reactants. Contained in the etherification zone is an etherification catalyst which, upon contact with the alcohol and isoalkene and normal alkene hydrocarbons, will produce the ether product. A wide range of materials are known to be effective as etherification catalysts for the isoalkene reactants including mineral acids such as sulfuric acid, boron trifluoride, phosphoric acid on kieselguhr, phosphorous-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. A particularly preferred etherification catalyst is a macroporous acid-form of a sulfonic ion exchange resin such as a sulfonated styrene-divinylbenzene resin as described in U.S. Pat. No. 2,922,822 having a degree of crosslinking of about 5 to 60%. Suitable resins are available commercially. Specialized resins have been described in the art and include copolymers of sulfonyl fluorovinyl ether and fluorocarbons as described in U.S. Pat. No. 3,489,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least about 400 $m^2$/g, a pore volume of about 0.6–2.5 ml/g and a mean pore diameter of 40–1000 Angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929.

A wide range of operating conditions are employed in processes for producing ethers from olefins and alcohols. Many of these include vapor, liquid, or mixed-phase operations. Processes operating with vapor or mixed-phase conditions may be suitably employed in this invention. In a preferred embodiment, liquid phase conditions are used.

The range of etherification conditions for processes operating in liquid phase still includes a broad range of suitable conditions including a superatmospheric pressure sufficient to maintain the reactants as liquid phase, generally below about 700 psig, and a temperature between about 85° F. and about 210° F. Even in the presence of additional light materials, pressures in the range of about 140 to 580 psig are sufficient. A preferred temperature range is about 100°–210° F. The reaction rate is normally faster at higher temperatures, but conversion is more complete at lower temperatures due to favorable thermodynamics equilibrium. High conversion in a moderate volume reaction zone can, therefore, be obtained if the initial section of the reaction zone, e.g., the first two thirds, is maintained above 160° F. and the remainder of the reaction zone is maintained below 120° F. This may be accomplished most easily with two reactors. The ratio of alcohol to isoolefin should normally be maintained in the range of about 1:1 to 2:1, preferably 1.05:1 and 1.5:1. An excess of methanol, above that required to achieve satisfactory conversion at good selectivity, should be avoided as some decomposition of methanol to dimethyl ether (DME) may occur which may increase the load on downstream separation facilities. A description of suitable etherification processes useful for the present invention can be found in U.S. Pat. Nos. 4,219,678 to Obenaus et at. and U.S. Pat. No. 4,282,389 to Droste et at. which are incorporated herein.

The etherification zone operates selectively to principally convert only the tertiary olefins. Therefore, alkanes and normal alkenes pass through the etherification zone without any significant conversion to products or by-products. Thus, the etherification zone effluent together with the unreacted feed components provides a stream of ether product and normal and branched alkenes and alkane isomers for separation.

The effluent from the etherification reaction exits the etherification reaction zone and enters a separation zone. The separation zone can be any zone known to those skilled in the art for separating a hydrocarbon feed stream into its various fractions. In a preferred embodiment, the arrangement of the separation zone typically consists of at least one distillation zone. In this distillation zone, a low boiling fraction comprising isoalkane and alcohol can be removed from the overhead stream of the distillation zone. In addition, the overhead stream can contain a normal alkene that was not reacted in the etherification zone and a normal alkane that entered the etherification zone as part of the hydrocarbon feed stream of the present invention. A high boiling fraction that principally comprises the ether product can be removed from the bottoms portion of the distillation zone.

A useful arrangement for the separation zone of this invention is the use of a reactive distillation zone that contains a bed of etherification catalyst. The distillation zone can provide additional etherification of unreacted isobutene. Accordingly, the reactive distillation zone can be used as a combined reactor. Processes for the production of ethers by reactive distillation are taught in U.S. Pat. Nos. 3,634,535 and 4,950,803. The operating conditions employed in the reactive distillation zone are generally the same as those outlined herein for the etherification reaction zone. No particular apparatus or arrangement is needed to retain the catalyst bed within the distillation section of the reactive distillation zone and a variety of methods can be used to incorporate the bed or region of catalyst within the reactive distillation zone. For example, the catalyst may be retained between suitable packing materials or may be incorporated onto a distillation tray itself. A preferred method of retaining the catalyst is through the use of a corrugated structural device that is described in U.S. Pat. No. 5,073,236 which is hereby incorporated by reference.

The ether product exits the bottom of the reactive distillation zone and is recovered. The overhead raffinate stream from the reactive distillation zone comprising an isoalkane, a normal alkane, a normal alkene, a small amount of unreacted isoalkene, a small amount of unreacted alcohol, and side reaction products can be passed to an alcohol recovery section.

An essential feature of the present invention is recycling an etherification sidecut stream from the separation zone to the etherification zone. This sidecut stream is characterized by a Recycle Quotient which is defined as:

$$\text{Recycle Quotient} = \frac{\frac{I\text{ recy}}{E\text{ recy}}}{\frac{I\text{ eq}}{E''\text{ eq}}} > 1$$

where:

I recy=molar concentration of isoalkene in the etherification sidecut stream

E recy=molar concentration of tertiary ether in the etherification sidecut stream I effl=molar concentration of isoalkene in the etherification effluent stream E effl=molar concentration of tertiary ether in the etherification effluent stream;

In a preferred embodiment, the Recycle Quotient ranges from about 1.0 to 15, preferably 1.5 to 5.0. In a preferred embodiment, the denominator of the Recycle Quotient (I effl/E effl) is equal to the ratio of the reaction equilibrium condition values, i.e., I eq/E eq.

The etherification sidecut stream can also be characterized in terms of absolute isoalkene concentration. The greater the isoalkene concentration in the etherification sidecut stream the less the volume of etherification sidecut stream required to increase isoalkene conversion to ether. Accordingly, in a preferred embodiment, the isoalkene concentration in the etherification sidecut stream ranges from about 2–70 mole %, preferably about 5–20 mole %.

The etherification sidecut stream can be liquid, vapor, or a mixture thereof. In a preferred embodiment, the etherification sidecut stream is a vapor stream. The reason is the ratio of isoalkene to tertiary ether molar concentration in the vapor phase is higher than the ratio of the isoalkene to tertiary ether molar concentration in the liquid phase.

The exact amount of the sidecut stream that is to be recycled to the etherification zone will vary depending upon the concentrations of isoalkene and tertiary ether contained in the sidecut stream. The higher the concentrations, the lower the amount of recycle required to effect a given conversion increase.

Referring to FIG. 1, a combined feed stream comprising isopentene, methanol, isopentane and normal pentene enters an etherification reactor 4 via line 2. Etherification reactor 4 is operated at a temperature of about 143° F. and a pressure of about 60 psi. In etherification reactor 4, the isopentene is reacted with the methanol to form tertiary amyl methyl ether (TAME).

After exiting etherification reactor 4, the etherification reactor effluent is passed to reactive distillation column 8 through line 6. Reactive distillation column 8 has a diameter of about 3–15 feet. The top 16 and bottom 18 sections of column 8 are fractionation zones. The middle section 10 of column 8 is a reaction zone filled with 0–50 feet of etherification catalyst/distillation packing. Operating conditions for column 8 include a temperature of about 120°–195° F. and a pressure of about 15–60 psia. The feed to column 8 is introduced at a point below reaction zone 10. A suitable reflux ratio for column 8 is about 0.6–2.0. Reflux ratio is defined as the amount of overhead liquid recycled back to the distillation tower to the amount of overhead liquid that is recovered as distillate.

Exiting the top section 16 of reactive distillation column 8 at a temperature of about 110°–150° F. and a pressure of about 15–60 psia by line 12 is an overhead raffinate stream that predominantly contains methanol, isopentane, non-tertiary pentenes and normal pentane. Exiting the bottom section 18 of reactive distillation column 8 at a temperature of about 250°–300° F. and a pressure of about 15–60 psia via line 14 is a bottoms product stream that comprises about 90–100 mole % TAME.

Exiting from the bottom fractionation section 18 of reactive distillation column 8 by line 15 at a point below the feed is an etherification recycle vapor stream. The recycle ratio (defined as the ratio of the flow rate of the sidecut stream to the flow rate of the fresh feed stream) is about 0.4–1.2. The etherification sidecut stream exits column 8 and contains isoamylene, isopentane, normal, pentane non-tertiary pentenes and TAME. The sidecut stream is characterized by an isoamylene concentration of about 7–20 mole % and an isoamylene to TAME molar ratio of about 2:1 to 4:1.

This vapor sidecut stream is then cooled and pumped back to etherification reactor 4. The heat from the vapor sidecut stream is recovered.

EXAMPLES—INTRODUCTION

All five of the following examples were based on computer simulations. The purpose of Examples 1–4 is to determine the effect of recycling an etherification sidecut stream to the etherification reactor has on conversion of isoamylene to TAME. The purpose of Example 5 is to determine the effect of phase of the etherification sidecut stream on the conversion of isoamylene to TAME.

The results showed that recycling an etherification stream selected from a location along the length of the reactive distillation tower such that the isoamylene concentration and the isoamylene to TAME ratio were relatively high increased the conversion of the isoamylene to TAME in comparison to the no recycle case (See Table 1). Further, the results showed that recycling a vaporous etherification sidecut stream increased conversion of isoamylene to TAME in comparison to the liquid recycle case (See Table 2).

Example 1 is a simulation of a no sidecut stream case. The remaining examples involve recycle of a sidecut stream from the reactive distillation column to the etherification reactor. Example 2 is a simulation of a recycle case. Example 3 is simulation of a recycle case using ten (10) additional feet of reactive distillation packing Example 4 is a simulation of a recycle case using ten (10) additional feet of reactive distillation packing and using an increased reflux ratio. Example 5 is a comparative example simulating vapor and liquid etherification sidecut streams.

In Examples 1–5, a $C_5$ hydrocarbon (coming isoamylene) stream was contacted with methanol in the presence of an etherification catalyst in at least one etherification reactor at etherification conditions to produce an etherification effluent. The etherification effluent was then passed to a reactive distillation column having a diameter of about 8 feet and three (3) sections. The top and bottom sections of the column were fractionation zones. The middle section of the column was a reaction zone filled with 0–40 feet of etherification catalyst/distillation packing. The reactive distillation column configuration consisted of 10 and 25 equilibrium stages for the top and bottom fractionation sections, respectively, and 0–40 feet of etherification catalyst/distillation packing for the reactive distillation zone.

Figure 2:
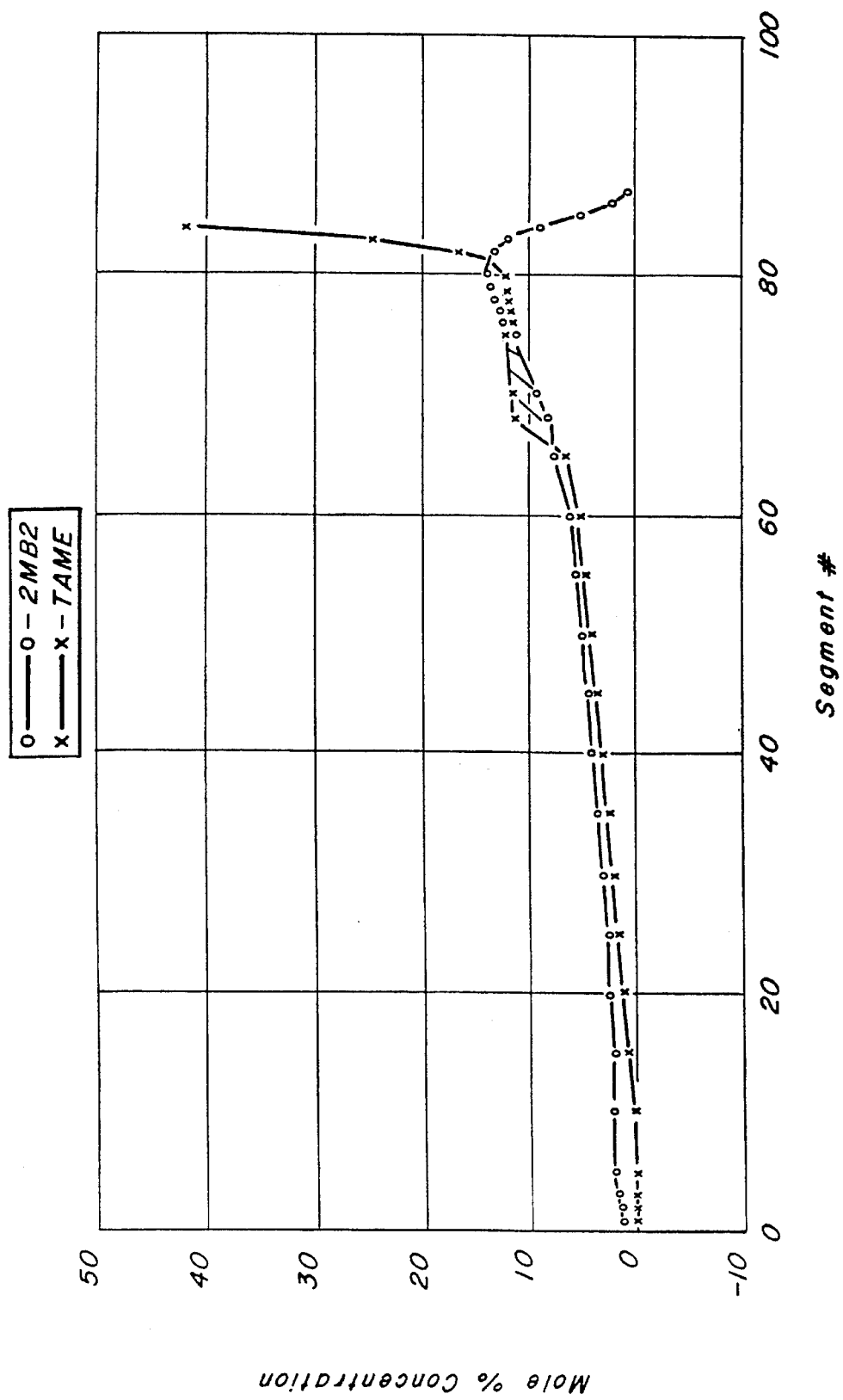
FIG. 2 is a plot of isoamylene and TAME concentration in the liquid phase versus segments (equilibrium stages) along the length of a reactive distillation column.
Figure 3:
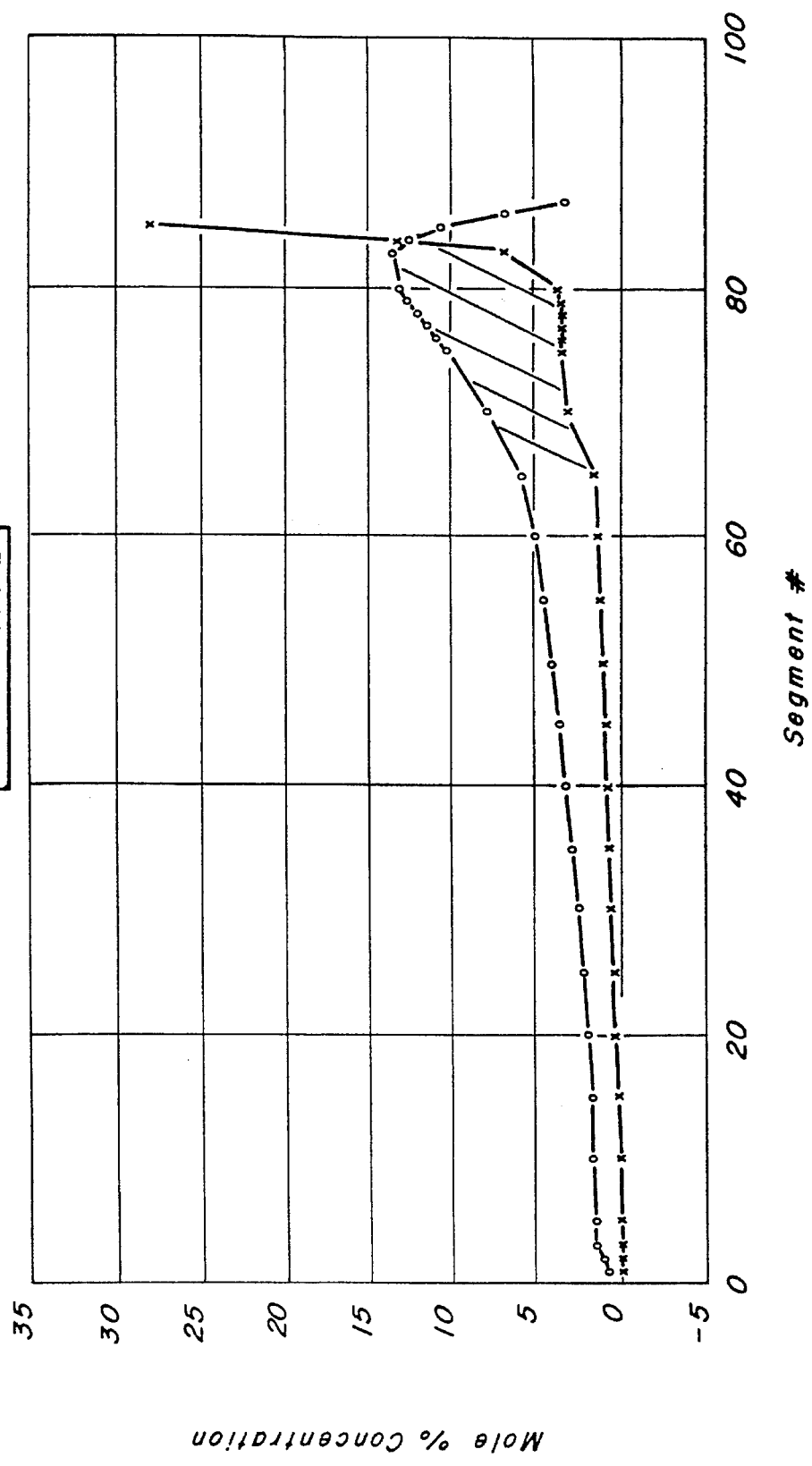
FIG. 3 is a plot of isoamylene and TAME concentration in the vapor phase versus segments (equilibrium stages) along the length of a reactive distillation column.

FIGS. 2 and 3 are plots of isoamylene and TAME concentrations versus discrete segmental units along the length of the reactive distillation column. A segment is defined as one theoretical tray for the fractionation sections of the reactive distillation column and as 0.6–0.8 feet for the catalyst section of the reactive distillation column. The first 10 segments correspond to the top fractionation section of the reactive distillation column. The next 50 segments correspond to the catalyst section of the column. The final 25 segments correspond to the bottom section of the reactive distillation column. The vertical axis of each figure represents the isoamylene and TAME concentrations. The horizontal axis of each figure represents the location along the length (in segments) of the reactive distillation column. The left side of the horizontal axis corresponds to the top section of the reactive distillation column and the right side of the horizontal axis corresponds to the bottom section of the reactive distillation column.

The purpose of FIGS. 2 and 3 is to generally show how the concentration of isoamylene and TAME vary along the length of the reactive distillation column. Near the top section of the column, the isoamylene concentration is low and isoamylene to TAME ether mole ratio is high. However, near the bottom of the column the isoamylene concentration and isoamylene to TAME mole ratio are much higher. Note that at some point along the bottom of the reactive distillation column the concentration of TAME increases dramatically and the concentration of isoamylene drops sharply.

More specifically, the purpose of FIGS. 2 and 3 is to generally indicate where along the length of the column the etherification sidecut stream is selected for the upcoming examples. The crossed-hatched areas of the plots in FIGS. 2 and 3 represent the positions along the length of the reactive distillation column at which both the isoamylene concentration and the isoamylene to TAME mole ratios are high. A comparison of FIGS. 2 and 3 illustrates that the cross-hatched area for FIG. 3 is much larger than that for FIG. 2. In other words, the isoamylene to TAME mole ratio for a vapor etherification sidecut stream is larger than that for a liquid etherification stream.

Further with respect to FIGS. 2 and 3, it is important to note that if the etherification sidecut streams had been selected from a location along the length of the column represented by points along the curves that fell outside the crossed-hatched area (for example near the top of the column), then an excessive volume of the etherification sidecut stream would be required to significantly improve the conversion of isoamylene and methanol to TAME. Such a large recycle rate would make the process extremely energy intensive.

EXAMPLE 1

In Example 1, a low recycle case was simulated. In this example, an etherification input stream comprising $C_5$ hydrocarbons was mixed with methanol to form a combined stream that was fed to a fixed bed etherification reactor. The combined stream contained mostly methanol and isopentane. The combined feed also contained some isopentene and normal pentane. The fixed bed etherification reactor was operated at a temperature of about 153° F. and a pressure of about 49 psi. In the fixed bed etherification reactor, it was assumed that the reaction of isopentene with methanol to form tertiary amyl methyl ether proceeded to equilibrium.

Exiting the fixed bed etherification reactor was the etherification reactor effluent that contained mostly methanol, isopentane and normal pentane. The etherification effluent also contained TAME and isopentene. The isopentene to TAME ratio for Example 1 was about 0.48. The etherification effluent stream was then passed to a reactive distillation column.

Operating conditions for the reactive distillation column included a temperature of about 130° F. and a pressure of about 45 psi at the top of the column and a temperature of about 259° F. and a pressure of about 51 psi at the bottom of the column. The column had a reflux ratio of 1.4.

Exiting the top of the reactive distillation column at a temperature of about 130° F. and a pressure of about 39 psi was an overhead raffinate stream that contained mostly isopentane, normal pentane and methanol. The overhead raffinate stream also contained a small amount of isopentene. Exiting the bottom of the reactive distillation column at a temperature of about 259° F. and a pressure of about 52 psi was a bottoms product stream that was made up largely as TAME.

Exiting the bottom fractionation zone of the reactive distillation column at a very low rate and at a temperature of about 178° F. and a pressure of about 50 psi was a sidecut stream that contained mostly normal pentane, TAME and isopentene. The sidecut stream contained some isopentane and a very small amount of methanol. The mole ratio of isopentene to TAME product in the sidecut stream was about 1.5. The recycle rate (defined as the ratio of flow rate of sidecut stream to the flow rate overhead raffinate stream) was about 0.0032.

The results of Example 1 are summarized in Table 1. As shown, the conversion for Example 1 was 90.6.

TABLE 1

| Case | Recycle/ Distillate | Catalyst Packing | Reflux | Utilities MMBTU/hr | Fixed Bed Conv | RWD Conv | Total Conv |
|---|---|---|---|---|---|---|---|
| 1 | .0032 | Yes | 1.4 | 25 | 67.9 | 71.1 | 90.6 |
| 2 | .67 | Yes | 1.4 | 30 | 71.4 | 74.8 | 95.8 |
| 3 | 1.0 | Yes | 1.8 | 36.2 | 70.0 | 83.8 | 97.7 |
| 4 | 1.0 | Yes | 2.1 | 39.5 | 70.1 | 86.1 | 96.1 |

EXAMPLE 2

In Example 2, a high recycle case was simulated. In this example, an etherification input stream comprising $C_5$ hydrocarbons was mixed with methanol to form a combined stream that was fed through a first fixed bed reactor, a first feed stream mixer, a feed stream cooler, a second fixed bed etherification reactor, a second feed stream cooler, and a reactive distillation column. The combined stream primarily contained methanol isopentane, isopentene and normal pentane.

The first fixed bed etherification reactor was operated at a temperature of about 143° F. and a pressure of about 60 psi. In the first fixed bed etherification reactor, it was assumed that the reaction of isopentene with methanol to form tertiary amyl methyl ether proceeded to equilibrium.

The effluent from the first fixed bed etherification reactor was then sent to a first mixer and a feed cooler. This effluent primarily contained isopentane and normal pentane. This effluent also contained some methanol and TAME, and a small amount of isopentene. The feed cooler reduced the temperature of the first reactor effluent from about 143° F. to about 120° F.

The cooler effluent was then passed to the second etherification reactor that was operated at a temperature of about 123° F. and a pressure of about 60 psi. The effluent from the second etherification reactor primarily contained isopentane and normal pentane. This effluent also contained some methanol and TAME, and a small amount of isopentene. The isopentene to TAME ratio for the second etherification reactor effluent was less than about 0.31. Next, the effluent from the second etherification reactor was passed to a second mixer prior to being directed to the reactive distillation column.

Operating conditions for the reactive distillation column included a temperature of about 130° F. and a pressure of about 39 psi at the top of the column and a temperature of about 266° F. and a pressure of about 52 psia at the bottom of the column, The column had a reflux ratio of 1.4.

Exiting the top of the reactive distillation column at a temperature of about 130° F. and a pressure of about 39 psi was an overhead raffinate stream that primarily contained isopentane. The overhead raffinate also contained some methanol and normal pentane. Exiting the bottom of the reactive distillation column at a temperature of about 266° F. and a pressure of about 52 psi was a bottom product stream that was primarily made up of TAME.

Exiting from the bottom fractionation section of the reactive distillation column at a relatively high flow rate and at a temperature of about 175° F. and a pressure of about 60 psi was a sidecut stream that primarily contained normal pentane. This sidecut stream also contained some TAME, isopentene (isoamylene) and isopentane The mole ratio of isopentene to TAME product in the sidecut stream was about 0.76. The recycle/distillate flow rate was about 0.67.

The results of Example 2 are summarized in Table 1. As shown, the conversion for Example 2 was 95.8%, an increase of 6% over the low recycle rate base case of Example 1.

EXAMPLE 3

In Example 3, a high recycle rate case was simulated with an additional 10 feet (total of 40 feet) of etherification catalyst/distillation packing in comparison to Examples 1 and 2. In this example, an etherification input stream comprising $C_5$ hydrocarbons was mixed with methanol to form a combined stream that was fed through a first fixed bed reactor, a first feed stream mixer, a feed stream cooler, a second fixed bed etherification reactor, a second feed stream cooler, and a reactive distillation column. The feed stream primarily contained methanol and isopentane. The feed stream also contained some isopentene and normal pentane.

The first fixed bed etherification reactor was operated at a temperature of about 138° F. and a pressure of about 60 psi. In the fixed bed etherification reactor, it was assumed that the reaction of isopentene with methanol to form tertiary amyl methyl ether proceeded to equilibrium.

The effluent from the first fixed bed etherification reactor was then sent to a first mixer and a feed cooler. This effluent primarily contained isopentane and normal pentane. This effluent also contained some methanol and TAME, and a small mount of isopentene. The feed cooler reduced the temperature of the first reactor effluent from about 138° F. to about 12° F.

The feed cooler effluent was then passed to the second etherification reactor that was operated at a temperature of about 122° F. and a pressure of about 60 psi. The effluent from the second etherification reactor primarily contained isopentane and normal pentane. This effluent also contained some methanol and TAME, and a small mount of isopentene. The isopentene to TAME ratio for the second etherification reactor effluent was about 0.32. Next the effluent from the second etherification reactor was passed to the reactive distillation column.

Operating conditions for the reactive distillation column included a temperature of about 130° F. and a pressure of about 39 psi at the top of the column and a temperature of about 264° F. and a pressure of about 52 psi at the bottom of the column. The column had a reflux ratio of 1.8.

Exiting the top of the reactive distillation column at a temperature of about 130° F. and a pressure of about 39 psi was an overhead raffinate stream that primarily contained methanol, isopentane and normal pentane. This overhead raffinate stream also contained a very small amount of isopentene. Exiting the bottom of the reactive distillation column at a temperature of about 264° F. and a pressure of about 52 psi was a bottoms product stream that was made up mostly of TAME.

Exiting from the bottom fractionation section of the reactive distillation column in the liquid sidedraw recycle at a relatively high flow rate and at conditions including a temperature of about 175° F. and a pressure of about 60 psi was a sidecut stream that primarily contained isopentane and normal pentane. This sidecut stream also contained some isopentene and TAME, and a very small amount of methanol. Accordingly the mole ratio of isopentene to TAME product in the sidecut stream was less than about 0.81. The recycle/distillate rate was about 1.0.

The results of Example 3 are summarized in Table 1. As shown, the conversion for Example 3 was 97.8%, an increase of 8% over the low recycle rate base case of Example 1.

EXAMPLE 4

In Example 4, a high recycle rate case was simulated with an additional 10 feet (total 40 ft.) of etherification catalyst/ distillation packing in comparison to Examples 1 and 2, and with an increased reflux ratio in comparison to Example 3. In Example 4, an etherification input stream comprising $C_5$ hydrocarbons was mixed with methanol to form a combined stream that was fed through a first fixed bed reactor, a first feed stream mixer, a feed stream cooler, a second fixed bed etherification reactor, a second feed stream cooler, and a reactive distillation column. The combined feed primarily contained methanol and isopentane. The combined feed also contained some isopentene and normal pentane. The first fixed bed etherification reactor was operated at a temperature of about 138° F. and a pressure of about 60 psi. In the fixed bed etherification reactor it was assumed that the reaction of isopentene with methanol to form tertiary amyl methyl ether proceeded to equilibrium.

The effluent from the first fixed bed etherification reactor was then sent to a first mixer and a feed cooler. This effluent primarily contained isopentane and normal pentane. This effluent also contained some methanol and TAME, and a small amount of isopentane. The feed cooler reduced the temperature of the first reactor effluent from about 138° F. to about 120° F.

The feed cooler effluent was then passed to the second etherification reactor that was operated at a temperature of about 123° F. and a pressure of about 60 psi. The effluent from the second etherification reactor primarily contained isopentane and normal pentane. The effluent stream also contained some methanol and TAME. The isopentene to TAME ratio for the second etherification reactor effluent was less than about 0.31. Next, the effluent from the second etherification reactor was passed to the reactive distillation Operating conditions for the column included a temperature of about 130° F. and a pressure of about 39 psi at the top of the column and a temperature of about 264° F. and a pressure of about 52 psi at the bottom of the column. The column had a reflux ratio of 2:1.

Exiting the top of the reactive distillation column at a temperature of about 130° F. and a pressure of about 39 psi was an overhead raffinate stream that primarily contained isopentane. This overhead raffinate stream contained methanol and normal pentane. Exiting the bottom of the reactive distillation column at a temperature of about 264° F. and a pressure of about 52 psi was a bottoms product stream that was made up mostly of TAME.

Exiting from the bottom fractionation section of the reactive distillation column at a relatively high flow rate and at conditions including a temperature of about 175° F. and a pressure of about 60 psi was a sidecut stream that primarily contained normal pentane and isopentane. The sidecut stream also contained some isopentene and TAME. The mole ratio of isopentene to TAME product in the sidecut stream was about 0.79. The recycle/distillate rate was about 1.0.

The results of Example 4 are summarized in Table 1. As shown, the conversion for Example 4 was 98.1%, an increase of 8.3% over the low recycle rate base case of Example 1.

EXAMPLE 5

In Example 5, a comparison was made between two (2) groups of four (4) runs each. In the first group (Runs A1–A4), the sidecut sidecut stream was liquid. In the second group (Runs B1–B4), the sidecut sidecut stream was vapor. All eight (8) runs were simulated using one adiabatic reactor and one reactive distillation column, In all of the runs except A1 and B1, the reactive distillation column contained 30 feet of etherification catalyst/distillation packing.

The results of Example 5 are shown below in Table 2.

TABLE 2

EFFECT OF VAPOR PHASE AND LIQUID PHASE SIDECUT RECYCLE ON CONVERSION

| Case | Recycle/Feed | Recycle Phase | Catalyst Packing | Reflux | Utilities MMBTU/hr | Conversion |
|------|--------------|---------------|------------------|--------|--------------------|------------|
| A1   | 1.0          | L             | No               | 1.4    | 31.7               | 85.0       |
| A2   | .33          | L             | Yes              | 1.4    | 28.0               | 93.7       |
| A3   | .66          | L             | Yes              | 1.4    | 28.6               | 94.2       |
| A4   | 1.0          | L             | Yes              | 1.4    | 29.0               | 94.3       |
| B1   | 1.0          | V             | No               | 1.4    | 40.1               | 89.7       |
| B2   | .33          | V             | Yes              | 1.4    | 30.5               | 94.1       |
| B3   | .66          | V             | Yes              | 1.4    | 33.9               | 95.1       |
| B4   | 1.0          | V             | Yes              | 1.4    | 37.2               | 95.7       |

These results show that in all cases where the phase of the sidecut sidecut stream was vapor, the conversion of isoamylene to TAME was higher than the conversion for the liquid sidecut sidecut stream.

What is claimed:

1. A process for the production of tertiary amyl methyl ether (TAME) by etherification which comprises the steps:

(a) passing a feed stream, comprising methanol, isopentane and isopentene, and a recycle stream into an etherification reaction zone and producing a reaction zone effluent stream comprising TAME, isopentane, isopentene and methanol;

(b) passing the reaction zone effluent stream into a catalytic distillation column having top and bottom fractionation zones and a middle zone of etherification catalyst at a point below the etherification catalyst;

(c) recovering a net overhead stream comprising isopentane from overhead vapors removed from the catalytic distillation column;

(d) recovering a net bottoms stream comprising TAME from bottoms liquid removed from the catalytic distillation column;

(e) withdrawing a sidecut stream from the catalytic distillation column at a point within the catalytic distillation column below the point at which the reaction zone effluent stream enters the catalytic distillation column, with the sidecut stream comprising essentially isopentene and TAME, having an isopentene concentration of from about 5–20 mole % and having a higher molar ratio of isopentene to TAME than the reaction zone effluent stream, and passing the sidecut stream into the etherification reaction zone as the previously referred to recycle stream.

2. The process of claim 1 wherein the molar ratio of isopentane to TAME in the sidecut stream is from 1.5 to 5.0.

* * * * *